Figure 1:
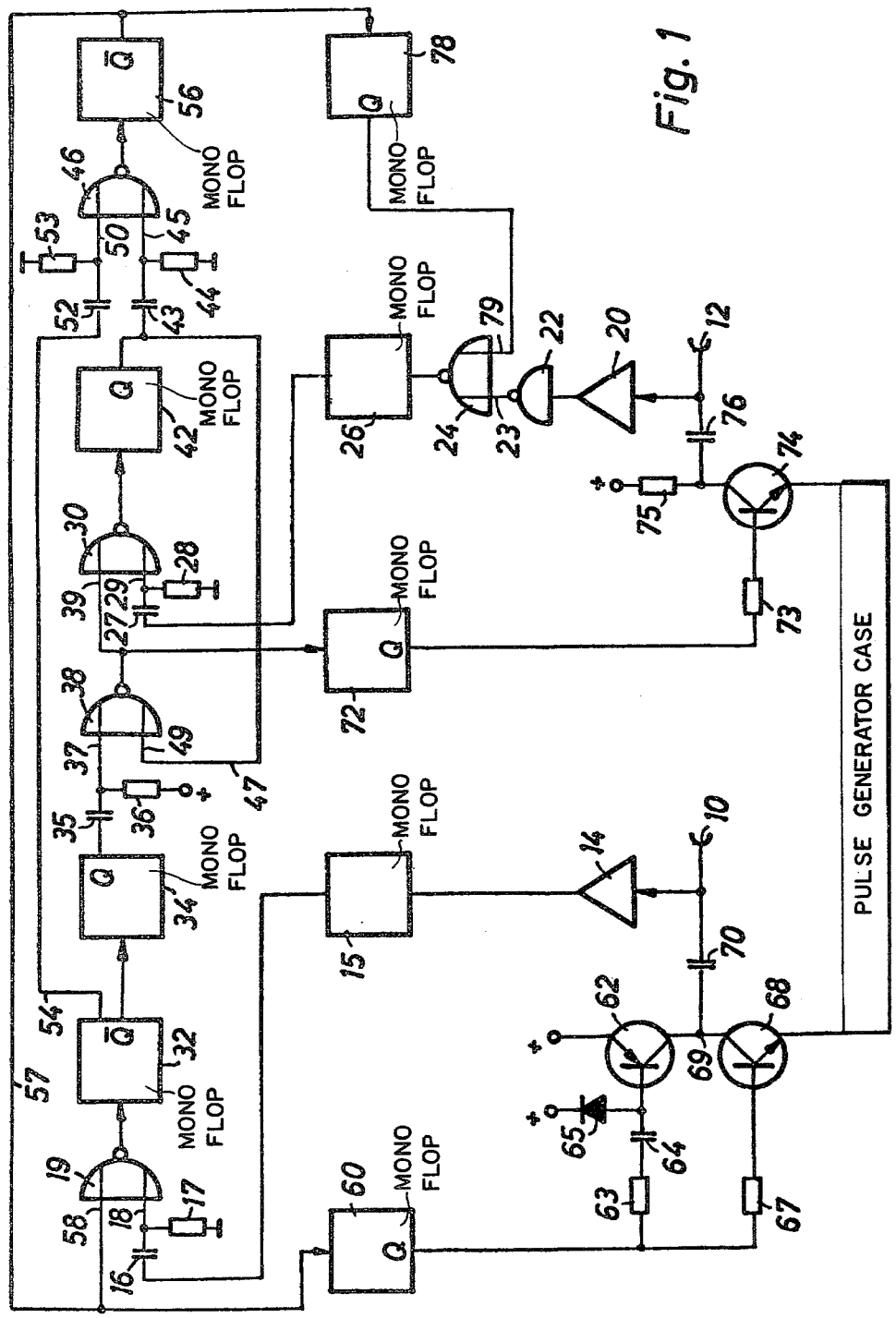

United States Patent [19]

Funke

[11] 4,312,355
[45] Jan. 26, 1982

[54] HEART PACEMAKER

[75] Inventor: Hermann D. Funke, Bonn, Fed. Rep. of Germany

[73] Assignee: Medtronic B.V., Kerkrade, Netherlands

[21] Appl. No.: 120,237

[22] Filed: Feb. 11, 1980

Related U.S. Application Data

[63] Continuation of Ser. No. 868,575, Jan. 11, 1978, abandoned, which is a continuation of Ser. No. 940,694, Sep. 8, 1978, abandoned.

[51] Int. Cl.³ .............................................. A61N 1/36
[52] U.S. Cl. ............................................. 128/419 PG
[58] Field of Search ....... 128/419 P, 419 PG, 419 PT

[56] References Cited

U.S. PATENT DOCUMENTS

| | | | |
|---|---|---|---|
| 3,709,229 | 1/1973 | Berkovits | 128/419 PG |
| 3,783,878 | 1/1974 | Thaler et al. | 128/419 PG |
| 3,830,242 | 8/1974 | Greatbatch | 128/419 PT |
| 3,867,949 | 2/1975 | Schwalm et al. | 128/419 PG |
| 3,943,936 | 3/1976 | Rasor et al. | 128/419 P |

OTHER PUBLICATIONS

Harthorng et al., "Boston Colloquium on Cardiac Pacing", Martinus Nijhoff Medical Division, The Hague, 1977, pp. 111-122.

*Primary Examiner*—William E. Kamm
*Attorney, Agent, or Firm*—Joseph F. Breimayer; Robert C. Beck

[57] ABSTRACT

A dual pace—dual sense cardiac pacemaker pulse generator having ventricular and atrial sensing and pulse generating means interconnected by circuit means to cause the atrium to be stimulated in the event that a natural atrial contraction is not sensed within a certain time from the last ventricular stimulus or natural contraction and the ventricle to be stimulated in the event that a naturally ventricular contraction is not sensed within a further time from the last atrial contraction or stimulus.

25 Claims, 2 Drawing Figures

HEART PACEMAKER

This is a continuation of application Ser. No. 868,575 filed Jan. 11, 1978 and now abandoned, and which is a continuation of application Ser. No. 940,694, filed Sept. 8, 1978, and now abandoned.

The present invention relates to an electric heart pacemaker more particularly circuit means for detecting and, if required, stimulating ventricular action, and circuit means for stimulating atrial action.

One type of known pacemaker of the above type disclosed in U.S. Pat. No. 3,595,242 entitled Atrial and Ventricular Pacemaker, the pacemaker monitors the ventricular endocardial ECG and as a function thereof programs both the atrial and the ventricular stimulation. A predetermined first time interval after the last QRS-complex an atrium stimulation, if required, is triggered, whereas at the end of a second predetermined time interval after the last QRS-complex the next ventricular stimulation is triggered. Accordingly both time periods for atrial and ventricular stimulation are defined by a common reference time, namely the last preceding ventricular action.

Pacemakers of the type outlined above are satisfactory to a limited extent only. In the case of a total AV-block e.g. the atrium and the ventricle are stimulated. In addition the pacemaker does not follow if the atrial rate increases.

Furthermore atrium controlled pacemakers are known in which the atrial depolarization is detected by an electrode positioned within or on the atrium and in which after a predetermined interval of e.g. 150 msec. a stimulating pulse is supplied to the ventricle. However, such pacemakers stimulate the ventricle only, whereas there is no atrial stimulation. On the other hand pacemakers are known which stimulate the atrium only because in certain types of diseases the atrium only beats slowly and stimulating of the atrium is sufficient to provide for a properly high ventricular rate. Such atrial pacemakers are to be hemodynamically preferred with respect to ventricular pacemakers because the sinus rhythm is maintained in the case of an intact AV-conduction and because the risk of embolism is substantially reduced. However, such an atrial stimulation is not applicable in the case of unreliable AV-conduction.

The heart activities within the atrium and the ventricle basically may be distinguished as to bradycardia and normal function in accordance with the following system: Atrium and ventricle beat at a sufficient rate (1st quadrant); the atrium is beating at an insufficient rate and must be stimulated whereas the ventricle properly follows (2nd quadrant); the atrium functions sufficiently, however, the ventricle does not follow (3rd quadrant); both the atrium and the ventricle require stimulation (4th quadrant). None of the prior pacemakers may be successfully used in all four bradycardia quadrants.

The object basic to the invention is to provide for a pacemaker which, if required, may stimulate the atrium and/or the ventricle and which is able to entrain the ventricle when the atrial rate increases. Accordingly the pacemaker should be able to provide for a correct function within all four aforementioned bradycardia quadrants.

Starting from a pacemaker of the type mentioned in the first paragraph this problem in accordance with the invention is solved by the provision of circuit means for detecting atrial action and further circuit means for triggering ventricular stimulation unless a spontaneous ventricular action follows within a first predetermined time interval after either a detected spontaneous or a stimulated atrial action, as well as circuit means for triggering an atrial action unless a spontaneous atrial action follows within a second predetermined time interval after either a detected spontaneous or a stimulated ventricular action.

The solution of the invention is based on the concept of completely electronically simulating the normally occurring heart cycle exteriorly of the heart and to force this external control cycle on the heart in the case of physiological disturbances which indicate the need for pacing within the atrium or the ventricle, wherein the heart, to the extent it functions properly, is able to suppress each individual partial function of the pacemaker. Accordingly the pacemaker may stimulate in the atrium only or in the ventricle only; it likewise may stimulate both within the atrium and the ventricle. If required an increased atrial rate is conducted to the ventricle. If required, i.e. in the case of all functions of the heart being undisturbed, neither the atrium nor the ventricle are stimulated.

Preferably the circuit means for triggering ventricular and atrial stimulation are interconnected so that the end of said first predetermined time interval triggers the beginning of said second predetermined time interval and that the end of said second predetermined time interval triggers the beginning of said first predetermined time interval. Accordingly a stimulating pulse is delivered to the ventricle if no ventricular contraction follows a spontaneous P-wave or a provoked atrial contraction within the predetermined first time interval. This pulse does not occur in the case of timely spontaneous ventricular activity. An atrial stimulating signal follows at the end of the second predetermined time interval after a ventricular pulse, irrespective of this ventricular pulse occurring spontaneously or being caused by pacemaker depolarization, unless a spontaneous atrial activity has been detected in due time.

Advantageously the circuit means for triggering ventricular stimulation and the circuit means for triggering atrial stimulation each include a monostable multivibrator which determines said first and said second predetermined time interval, respectively.

Preferably the first and the second predetermined time intervals are between 120 msec. and 200 msec. and between 600 msec. and 750 msec., respectively.

Preferably in each instance a unipolar electrode is provided for detecting and stimulating the atrial and the ventricular action, respectively, whereas the pacemaker pulse generator case constitutes the common neutral electrode.

According to a further development of the invention the circuit means for stimulating atrial action include an output capacitor adapted to be charged through first switch means and to be discharged through second switch means. This provides, after the output capacitor having been quickly charged, for a high input impedance of the atrial signal detecting circuit means and accordingly for an improved P-detection. If contrary thereto the circuit means for ventricular stimulation are designed in a conventional manner, a safe distinction between atrial and ventricular pulses in the ECG is possible. In this connection a particularly simple circuit arrangement is obtained in that an atrial stimulation triggering signal is adapted to control both switch means and that the charging switch means are preceded by time delay means. Thereby one and the same signal at first provides for the immediate triggering of the discharging switch means and for the correspondingly delayed subsequent actuation of the charging switch means.

Preferably the switch means for detecting ventricular action have associated thereto disabling means adapted to disable detection of ventricular action for a predetermined time period when an atrial stimulation is triggered.

For the purpose of testing suitably the first and/or the second time interval are adapted to be shortened.

In conformity with a further development of the invention the circuit means for detecting atrial action and/or the circuit means for detecting ventricular action comprise refractory means for blocking the detection of signals the frequency of which exceeds a predetermined maximum value. When such high-frequency noise signals are received, the circuit means for atrial and/or ventricular detection are disabled; the pacemaker will operate at fixed frequencies.

In the following the invention is further described in connection with preferred embodiments. In the attached drawings FIG. 1 illustrates a schematic wiring diagram of a first embodiment, and FIG. 2 illustrates a schematic wiring diagram of a modified second embodiment.

Figure 2:
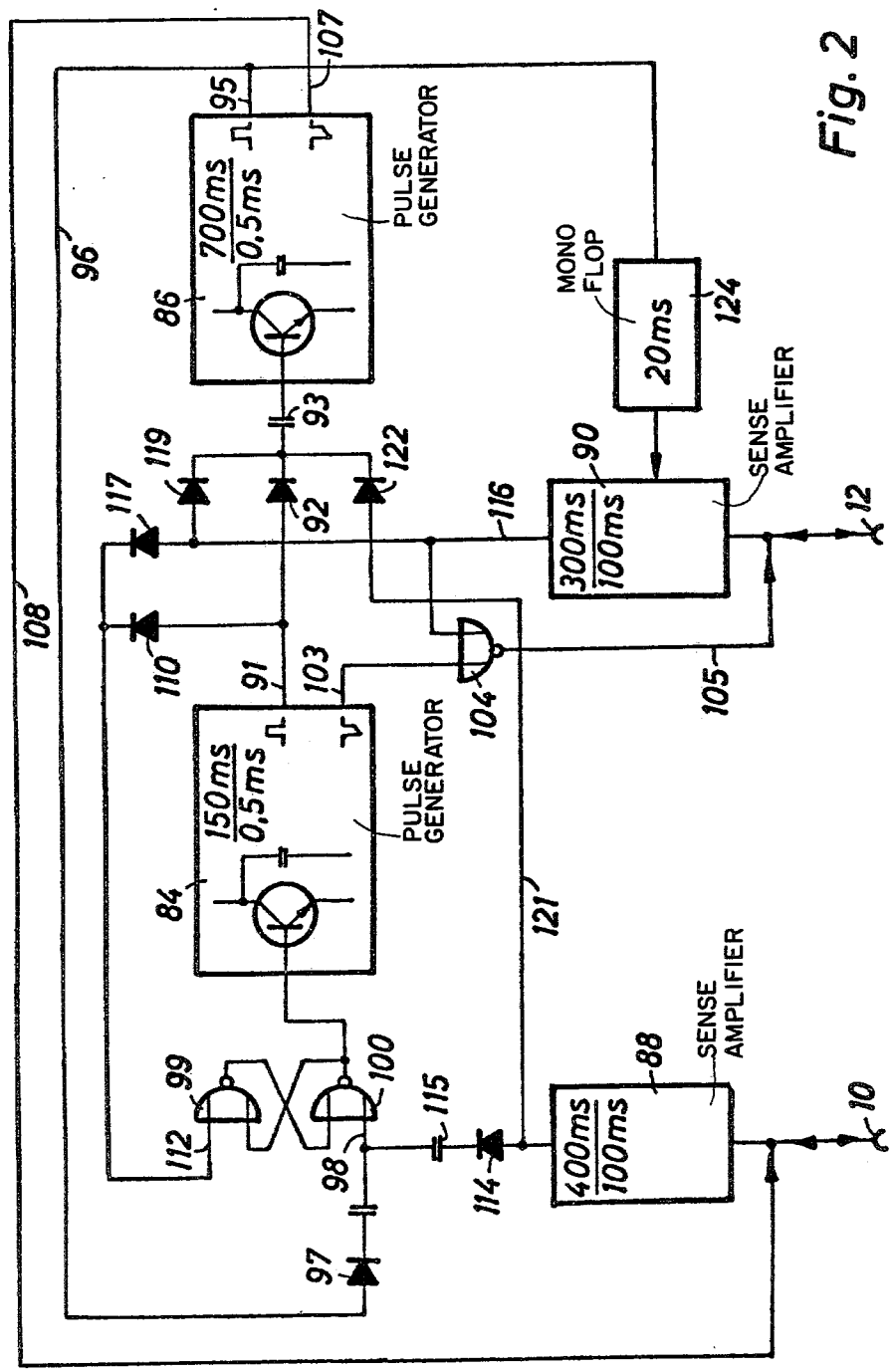

In the embodiment of FIG. 1 an electrode 10 is provided for supplying stimulating signals to the atrium and to detect natural atrium activity. In a similar manner an electrode 12 is adapted for connection to the ventricle to supply stimulating pulses thereto and to detect naturally occurring ventricle pulses. The atrium electrode 10 is connected to a first input 18 of a NOR-gate 19 through an atrium signal amplifier 14, a positive edge retriggering monoflop 15 provided for noise suppression and having a delay period of 100 msec., as well as through a differentiator consisting of a capacitor 16 and a resistor 17.

The ventricle electrode 12 communicates with a first input 23 of a NOR-gate 24 through a ventricle signal amplifier 20 and an inverter 22. The output of NOR-gate 24 is connected to a first input 29 of a NOR-gate 30 through a positive edge retriggering 100 msec. monoflop 26 and a differentiator consisting of a capacitor 27 and a resistor 28. Monoflop 26 is provided for noise suppression purposes.

The output of NOR-gate 19 is connected to the input of a negative edge triggering 400 msec. monoflop 32 defining a refractory period. The output of monoflop 32 is connected to the input of a negative edge triggering monoflop 34 having a delay period of 150 msec. Monoflop 34 defines the PQ-distance. Its output Q communicates through a differentiator defined by a capacitor 35 and a resistor 36, with a first input 37 of a NOR-gate 38. The output of NOR-gate 38 is connected to a second input 39 of NOR-gate 30.

The output of NOR-gate 30 is connected to the input of a negative edge triggering 300 msec. monoflop 42 defining a refractory period. The output Q of monoflop 42 is connected through a differentiator comprising a capacitor 43 and a resistor 44 to a first input of a NOR-gate 46. The output Q of monoflop 42 is further connected through a conduit 47 to a second input 49 of NOR-gate 38. A second input 50 of NOR-gate 46 is connected through a differentiator consisting of a capacitor 52 and a resistor 53 to a second output 54 of monoflop 32. The output of NOR-gate 46 is connected to the input of a negative edge retriggering monoflop 56 having a delay period of 700 ms and defining the QP-distance. The output Q of monoflop 56 is connected through a conduit 57 to a second input 58 of NOR-gate 19 and to the input of a positive edge triggering monoflop 60. Monoflop 60 has a delay period of 0.5 msec. and serves as a pulse shaper. The output Q of monoflop 60 is connected to the base of a PNP transistor 62 through the series connection of a resistor 63 and a capacitor 64. The base of transistor 62 is further connected through a diode 65 to the positive terminal of the voltage supply. In addition output Q of monoflop 60 is connected to the base of a NPN transistor 68 through a resistor 67. The emitter-collector paths of transistors 62 and 68 are connected in series between positive voltage and pulse generator case. The junction 69 of the collectors of transistors 62 and 68 is connected to one side of an output capacitor 70 the other side of which communicates with atrium electrode 10.

The input of a positive edge triggering pulse shaper monoflop 72 having a delay period of 0.5 msec. is connected to the output of NOR-gate 38. The output Q of monoflop 72 communicates through a resistor 73 with the base of an output transistor 74 the collector-emitter path of which is connected in series with a resistor 75 between positive supply voltage and pulse generator case. The collector of transistor 74 is connected to one side of an output capacitor 76, the other side of which communicates with ventricle electrode 12.

The output $\overline{Q}$ of monoflop 56 additionally is connected to the input of a positive edge triggering 40 msec. monoflop 78. The output Q of monoflop 78 is connected to a second input 79 of NOR-gate 24.

The circuit arrangement of FIG. 1 basically operates as follows:

At the input of monoflop 32 an information in the form of a pulse step appears when, through input 58 of NOR-gate 19, the information of the atrium having been stimulated is supplied, or when, through input 18 of gate 19, the information has been received that a spontaneous atrium activity has taken place. Accordingly a pulse step triggering the 400 msec. period always appears at the input of monoflop 32 when the atrium is depolarized by a stimulating pulse or when there is a spontaneous excitation of the atrium. Simultaneously with setting of monoflop 32 the input of monoflop 34 is triggered from the output Q of monoflop 32 thereby starting the 150 msec. period of monoflop 34. After the 150 msec. period of monoflop 34 having elapsed a pulse is delivered through the dynamic input 35,36, 37 of gate 38 to the output of this gate which pulse is supplied through the 0.5 msec. pulse shaper monoflop 72 to the conventionally designed ventricle stimulation output stage 73 to 76 and is supplied to the ventricle through electrode 12.

The pulse appearing at the output of gate 38 additionally is supplied to the input 39 of gate 30 and is passed to the input of monoflop 42. The pulse thereby starts the refractory period of 300 msec. Furthermore this pulse is supplied to the input 45 of gate 46 and to the input of monoflop 56 which is triggered. The 700 msec. delay period of monoflop 56 is started.

Similar to the conditions at the input of monoflop 32 an information appears at the input of monoflop 42 when a ventricle pulse has been delivered from the output of gate 38 or when an information characteristic of a spontaneous depolarization of the ventricle is received at gate 30. Accordingly it does not make any difference for the triggering of monoflop 42 whether the ventricle is stimulated or has been spontaneously activated. By the appeearence of a pulse step at the input of monoflop 42 the retriggerable monoflop 56 is again started. Therefore 700 msec. must elapse after a ventricle depolarization, irrespective whether it occured spontaneously or by stimulating, before the output Q of monoflop 56 goes low and an atrium pulse is delivered through conduit 57.

If the atrium activity spontaneously becomes faster than the rate corresponding to the intervention frequency of the pacemaker, the P-wave upon having been amplified in the atrium signal amplifier 14 again enters monoflop 32 through input 18 of gate 19. The respective pulse is delivered from the output 54 of monoflop 32 to the dynamic input 50 of gate 46. The pulse is transferred from gate 46 to monoflop 56. Accordingly at first no further atrium pulse can be delivered after a spontaneous atrium pulse for a period of at least 700 msec (the delay period of monoflop 56). Because this spontaneous atrium pulse again activates the ventricle through monoflop 34 after 150 msec. and the monoflop 56 is retriggered through gates 38 and 30 and monoflop 42, the atrium in fact is not again triggered before a period of 700 msec. +150 msec. =850 msec. has elapsed after a spontaneous P-wave.

An atrium pulse should result in a ventricle depolarization after 150 msec., i.e. the delay period of monoflop 34. However, it might be that this ventricle depolarization spontaneously occurs within the desired period. In this case the ventricle depolarizing pulse has no physiological function. Therefore it is desired to suppress this pulse in order to safe energy and for other reasons. For this purpose a feedback is provided from the output of monoflop 42 through conduit 47 to the input 49 of gate 38. The function of this feedback is as follows: If the 150 msec. pulse of monoflop 34 has nearly reached its end and in case a ventricle pulse therefore would be delivered to the ventricle through the output of gate 38, this is prevented by the ventricle activity having at this time again triggered the 300 msec. delay period at the input of monoflop 42. The potential appearing at the output Q of monoflop 42 now disables gate 38 through conduit 47. The pulse step appearing after the 150 msec. delay period of monoflop 34 therefore cannot be transferred to the ventricle through gate 38. Accordingly the unnecessary ventricle depolarization pulse does not occur if there was a spontaneous ventricle depolarization within the 150 msec. delay period.

In the following the mode of operation of the circuit arrangement of FIG. 1 in the four different bradycardia quadrants is described. At first it is assumed that the atrium as well as the ventricle beat at a sufficiently high rate and that therefore stimulation is not required (1st quadrant). The spontaneous P-signal received by the atrium electrode 10 is supplied to the input of monoflop 32 and, through the output 54 of monoflop 32 and the input 50 of gate 46, suppresses the delivery of a P-information through the output $\overline{Q}$ of monoflop 56, because monoflop 56 is retriggered. The timely occurring ventricle action in turn suppresses the delivery of a pulse to the ventricle by setting monoflop 42 through conduit 47 and input 49 of gate 38. Accordingly the atrium and the ventricle are not stimulated when the atrium activity occurs at a sufficiently high rate and when the ventricle responds in due time.

In the case of atrium bradycardia in which the atrium must be stimulated whereas the conduction to the ventricle is intact (2nd quadrant), the information that an atrium depolarization is to be effected by a pulse, is supplied to the input of monoflop 60 through the output $\overline{Q}$ of monoflop 56 and conduit 57 after termination of the 700 msec. delay period of monoflop 56 because in the meantime monoflop 56 is not retriggered. The 150 msec. delay period of monoflop 34 is started. Before this 150 msec. period has elapsed a spontaneous ventricle polarization occurs which is delivered to monoflop 42 through ventricle signal amplifier 20, gate 24, monoflop 26 and gate 30. Monoflop 42 is triggered and disables through conduit 47 the transfer of the ventricle stimulating pulse from output Q of monoflop 34 to monoflop 72. Thus the ventricle pulse is suppressed in retrograde.

If on the other hand the atrium beats at a sufficient and possibly substantially higher than normal rate up to a frequency of 150 beats/min., whereas the conduction to the ventricle is poor (3rd quadrant), the following happens: Spantaneous P-signals are delivered from the atrium electrode 10 to the input of monoflop 32 and start the 400 msec. refractory period defined by this monoflop. Simultaneously monoflop 34 is triggered. After the 150 msec. delay period of monoflop 34 the ventricle depolarization pulse is delivered through gate 38 and monoflop 72 to the ventricle output stage 73 to 76. When using the circuit parameters indicated for the embodiment of FIG. 1 the atrium rate may vary between 70 and 150 beats/min. (the latter corresponding to the 400 msec. refractory period of monoflop 32). The ventricle is entrained at the interval of the delay period of monoflop 34 (150 msec.). There is no atrium stimulation because monoflop 56 is retriggered after each spontaneous atrium pulse so that at first 700 msec. must elapse, and because after depolarization of the ventricle monoflop 56 is retriggered through the output of gate 30, monoflop 42 and the input 45 of gate 46. Accordingly an atrium pulse could not be delivered before 850 msec. (corresponding to the sum of the delay periods of monoflops 34 and 56) have elapsed. However, the atrium stimulation does not take place because the atrium has spontaneously functioned already before this time.

Finally, the case is considered that the atrium and the ventricle do not beat and therefore both must be stimulated (4th quadrant). Atrium stimulation now is effected in the manner outlined above. Because the ventricle does not follow within the desired 150 msec. period and because the 300 msec. delay period of monoflop 42 is not started through ventricle signal amplifier 20, gate 24 and monoflop 26 retrograde suppression of the pulse transfer through gate 38 does not take place. The pulse step occurring at the output of monoflop 34 after the end of the 150 msec. period appears at the input 37 of gate 38 and is delivered from the output of gate 38 through monoflop 72 to output stage 73 to 76. The ventricle is depolarized through ventricle electrode 12.

In order to provide for a safe detection of the ventricle complex following an atrium pulse, the 40 msec. monoflop 78 is triggered by the atrium stimulating pulse appearing at output $\overline{Q}$ of monoflop 56. This causes the transfer of the pulses sensed within the ventricle to be disabled through the input 79 of gate 24 during the delay period of monoflop 78. Atrium pulses received by the ventricle signal amplifier are prevented by this time slot from being effective in the ventricular circuit arrangement.

In the ventricular circuit arrangement the ventricle pulse is generated by quickly discharging the output capacitor 76 and slowly recharging this capacitor through resistor 75, whereas the dynamically connected transistor 62 is provided for recharging the atrium output capacitor 70. Recharging is effected through this transistor at a very low resistance and thus is terminated quickly. This ensures that less distortions occur in the ECG, that the atrium pulse may be easily distinguished in the ECG from the ventricle pulse and that upon the capacitor 70 being recharged the atrium signal amplifier has a substantially increased input impedance whereby P-sensing is further improved.

It is evident that output capacitor 76 likewise may be recharged through a transistor corresponding to transistor 62 in a low impedance manner. However, in view of the fact that the ventricle signal amplifier 20 operates in a reliable manner without any specific precautions being required, it normally will be preferable to provide for the described different design of the output stages to safely differentiate in the ECG the atrium pulse from the ventricle pulse to thereby facilitate the postoperative malfunction diagnosis.

In practice it is desirable to likewise check the pacemaker functions in cases in which the patient's natural rhythm is proper and the pacemaker is fully suppressed. This e.g. may be done by disabling the input amplifiers 14 and 20 through a magnetic switch and by waiting until the stimulating pulses coincide with stimulatible atrium and ventricle phases. Then it can be determined whether the atrium pulse provokes a P-wave and whether the ventricle pulse provokes a QRS-complex. As an alternative the PQ-delay period, which in the described embodiment amounts to 150 msec., may be drastically shortened to e.g. 50 msec. in order to bypass an intact conduction and to electrically stimulate the ventricle if the pacemaker is in proper condition. Simultaneously the delay period of monoflop 56 e.g. is shortened from 700 msec. to 450 msec. so that the sum of the delay periods of monoflops 34 and 56 is 500 msec. corresponding to a frequency of 120 beats/min. In this manner the heart is certainly overridden; the stimulation may be properly checked.

A circuit arrangement which basically corresponds to the circuit arrangement of FIG. 1 may be designed when using integrated circuits utilized for available demand pacemakers. Such an embodiment is illustrated in FIG. 2. It comprises a pair of integrated circuits 84 and 86. Each of circuits 84,86 includes a pulse generator having a timer adapted to be reset by spontaneous ventricle or atrium signals, respectively (corresponding to monoflop 56) as well as pulse shaping and output units (corresponding to monoflops 60 and 62 as well as to output stages 63 to 70 or 73 to 76, respectively). The refractory members 32 and 42, respectively, the noise suppression members 15 and 26, respectively, as well as the amplifiers 14 and 20, respectively are combined into integrated circuits 88 and 90, respectively.

The integrated circuits 84 and 86 are seriesly connected, a first output 91 tapped before the output unit of circuit 84 being connected through a diode 92 and a capacitor 93 to the input of integrated circuit 86. A first output 95 of integrated circuit 86 which corresponds to output 91 is connected through a conduit 96 and a diode 97 to an ON-input 98 of a storage member defined by a pair of mutually coupled NOR-gates 99,100, the output of this storage member being connected to the input of integrated circuit 84.

Input 98 functionally corresponds to the input of monoflop 32 of FIG. 1. At this junction an information is received whether a pacemaker pulse should stimulate the atrium or whether a spontaneous P-wave has occurred. Circuit 84 which is freely running at a frequency of 400 beats/min. corresponding to a pulse interval of 150 msec., is triggered through input 98 of storage member 99, 100, so that 150 msec. after the appearance of the P-information at the input 98 a stimulating pulse is transferred to the ventricle electrode 12 from the second output 103 of circuit 84 through a gate 104 and a conduit 105. The pacemaker thus operates as an atrium controlled ventricle pacemaker.

The circuit 86 which is freely running at a frequency corresponding to 700 msec. in the type of a normal demand pacemaker, is reset through the first output 91 of integrated circuit 84. Accordingly 700 msec. must elapse until an atrium pulse can be delivered to the atrium electrode 10 through the second output 107 of integrated circuit 86 and a conduit 108. Simultaneously an output pulse is fed back from output 95 of circuit 86 to the input 98 of storage member 99,100 whereby the generator of circuit 84 is restarted and a period of 150 msec. is triggered.

In view of the fact that a repetition rate corresponding to a 150 msec. pulse interval would not make sense, the OFF input 112 of storage member 99,100 is controlled from output 91 of circuit 84 through a diode 110 so that integrated circuit 84 is allowed to deliver each an individual pulse only. Therefore again an input signal at input 98 of storage member 99,100 is required to again trigger circuit 84 and to start the period of 150 msec.

The circuit arrangement of FIG. 2 operates in the four bradycardia quadrants as follows:

In the first quadrant—sufficient or fast atrium rate and quick response by spontaneous ventricle activities—the P-wave is received by the atrium electrode 10 and is supplied to the input 98 of storage member 99, 100 through integrated circuit 88, a decoupling diode 114 and a capacitor 115. The integrated circuit 84 is triggered and tends to deliver after 150 msec. through output 103 a pulse to the ventricle. However, because within this 150 msec. period integrated circuit 90 already has received through ventricle electrode 12 a spontaneous ventricle signal, a disabling signal is fed through a conduit 116 and a diode 117 to input 112 of storage member 99,100 and to one input of gate 104. The latter disables the transfer of the ventricle pulse from output 103 to ventricle electrode 12. Atrium pulses likewise cannot be delivered because the received ventricular response is supplied through integrated circuit 90 and a diode 119 to the input of integrated circuit 86 thereby resetting this circuit for 700 msec. The signal which after 150 msec. leaves output 91 of integrated circuit 84 is used to retrigger through diode 92 the 700 msec. period which already had been triggered through a conduit 121 and a diode 122. Therefore an interval of 850 msec. must elapse before a further atrium stimulating signal could be delivered. However, this delivery does not take place because the P-wave is received at a higher rate. Therefore the pacemaker remains inactive.

In the second quadrant, i.e. in case the atrium rate is to slow and the atrium requires stimulation, whereas conduction is effected in due time, a pulse is generated at the output 107 of integrated circuit 86 700 msec. after a P-signal. This pulse is supplied to the atrium through conduit 108. The ventricle depolarization occurring in this quadrant in due time causes the stimulating pulse which, in the manner outlined above, appears after 150 msec. at the output 103 of integrated circuit 84, to be prevented from passing through gate 104. Because the delay period of 700 msec. is retriggered from output 91 the atrium again is depolarized after a total of 850 msec. Again a ventricle response occurs in due time, which response, through the output of integrated circuit 90 and gate 104, hinders the ventricle pulse from being transferred from output 103 of integrated circuit 84 to the ventricle electrode 12.

In the case of sufficient or fast atrium activity and poor conduction (3rd quadrant) the pacemaker acts as an atrium controlled ventricular pacemaker. A P-wave reaches through integrated circuit 88 the input 98 and switches ON the storage member 99,100. The integrated circuit 84 is triggered and, after 150 msec., supplies a pulse to the ventricle through gate 104. This pulse can be transferred through gate 104 because there is no timely ventricle depolarization which would disable gate 104 through integrated circuit 90.

In the case of atrium bradycardia and ventricle bradycardia (4th quadrant) an atrium pulse is delivered from output 107 of integrated circuit 86. Simultaneously the storage member 99,100 is switched ON from output 95 through conduit 96 and diode 97, with the result that 150 msec. later a pulse appears at output 103 of integrated circuit 84. This pulse is transmitted through gate 104 to ventricle electrode 12 because at this time no ventricular contraction has taken place which would disable gate 104 through integrated circuit 90.

Similar to the circuit arrangement of FIG. 1 a circuit unit 124 is provided which e.g. is comprised of RC-members and the function of which corresponds to the function of monolfop 78. Circuit unit 124 inhibits the ventricle amplifier of integrated circuit 90 during an atrium pulse and a short time thereafter, e.g. a period of 20 msec., so that atrium pulses cannot be erroneously detected by the ventricle amplifier.

The atrium stimulation pulse output stage preferably may be designed in the manner outlined above in connection with FIG. 1 so that the output capacitor is quickly recharged thereby facilitating the detection of the P-signals and increasing the input impedance of the P-amplifier.

I claim:

1. Electric heart pacemaker comprising circuit means for detecting and, if required, stimulating ventricular action, circuit means for detecting and, if required, stimulating atrial action, and further circuit means for triggering ventricular stimulation unless a spontaneous ventricular action follows within a first predetermined time interval after either a detected spontaneous or a stimulated atrial action, as well as circuit means for triggering an atrial action unless a spontaneous atrial action follows within a second predetermined time interval after either a detected spontaneous or a stimulated ventricular action.

2. Pacemaker according to claim 1 wherein the circuit means for triggering ventricular and atrial stimulation further comprise means responsive to the end of said first predetermined time interval for triggering the beginning of said second predetermined time interval and responsive to the end of said second predetermined time interval for triggering the beginning of said first predetermined time interval.

3. Pacemaker according to claim 1 wherein the circuit means for triggering ventricular stimulation and the circuit means for triggering atrial stimulation each include a monostable multivibrator which determines said first and said second predetermined time interval, respectively.

4. Pacemaker according to claim 1 wherein said first predetermined time interval is between 120 msec. and 200 msec.

5. Pacemaker according to claim 1 wherein said second predetermined time interval is between 600 and 750 msec.

6. Pacemaker according to claim 1 further comprising a first unipolar electrode for detecting and stimulating atrial action, a second unipolar electrode for detecting and stimulating ventricular action, an electrically conductive pulse generator case and further circuit means for electrically connecting said case and said first electrode to said circuit means for stimulating and detecting atrial action and said case and said second electrode to said circuit means for stimulating and detecting ventricular action.

7. Pacemaker according to claim 1 wherein the circuit means for triggering atrial action includes an output capacitor and first and second switch means connected to said output capacitor and responsive to an atrial stimulation triggering signal provided by said circuit means for triggering atrial action for charging and discharging, respectively, said output capacitor.

8. Pacemaker according to claim 7 wherein the circuit means for triggering atrial action further comprises time delay means coupled to said first switch means for delaying the response of the first switch means to the atrial stimulation triggering signal and enabling the discharging and charging of the output capacitor sequentially through the second and first switching means, respectively.

9. Pacemaker according to claim 1 wherein the circuit means for detecting ventricular action further comprises disabling means responsive to said circuit means for stimulating atrial action for disabling said circuit means for detecting ventricular action for a predetermined time period when atrial stimulation is triggered.

10. Pacemaker according to claim 1 further comprising means for shortening said first and/or said second time intervals for testing purposes.

11. Pacemaker according to claim 1 wherein the circuit means for detecting atrial action and/or the circuit means for detecting ventricular action comprise refractory means for blocking the detection of signals recurring at rates exceeding predetermined maximum rates.

12. A cardiac pacemaker pulse generator comprising:
first terminal means adapted to being connected to the atrium of a heart;
second terminal means adapted to being connected to the ventricle of said heart;
first sensing means connected to said first terminal means for providing a signal whenever a signal indicative of an atrial contraction is applied to said first terminal;
second sensing means connected to said second terminal for providing a signal whenever a signal indicative of a ventricular contraction is applied to said second terminal; and
circuit means responsive to said first and second sensing means for providing pulse signals to said first and second terminal means in the absence of signals from said first and second sensing means within constant defined time intervals, said circuit means including first and second defined time interval determining means, said first defined time interval being the time between the occurrence of an atrial contraction and the provision of a pulse to said second terminal means and said second defined time interval being the time between the occurrence of a ventricular contraction and the provision of a pulse to said first terminal means.

13. The invention according to claim 12 wherein said atrial contraction and ventricular contractions can be either stimulated or natural.

14. The invention according to claim 12 wherein said circuit means includes means to disable said second sensing means for a portion of said first time interval whenever a pulse signal is provided to said first terminal.

15. The invention according to claim 12 wherein said circuit means includes means to prevent the provision of pulse signals to either one of said first and second terminals in response to a sensing means signal from the sensing means connected to that one terminal.

16. A dual pace-dual sense cardiac pacemaker pulse generator comprising:
a ventricular terminal adapted to being electrically coupled to the ventricle of the heart;
an atrial terminal adapted to being electrically coupled to the atrium of the heart;
ventricular sensing means for providing a signal in response to electric signals applied to said ventricular terminal which manifest natural ventricular contractions;
atrial sensing means for providing a signal in response to electrical signals applied to said atrial terminal which manifest natural atrial contractions;
ventricular pulse providing means for providing ventricular stimulating pulses to said ventricular terminal;
atrial pulse providing means for providing atrial stimulating pulses to said atrial terminal; and
circuit interconnect means for causing said ventricular pulse providing means to provide a ventricular stimulating pulse a first constant defined time after either a signal from said atrial sensing means or said atrial pulse providing means is provided unless a signal from said ventricular sensing means occurs prior in time, said circuit interconnect means further causing said atrial pulse providing means to provide an atrial stimulating pulse after the passage of a second constant defined time after either a ventricular signal was sensed or a ventricular stimulating pulse was applied to said ventricular terminal, unless a signal from said atrial sensing means occurs prior in time.

17. The invention according to claim 16 wherein said circuit means includes blanking means for inhibiting any response of said ventricular sensing means for a certain time, less than said first constant defined time, following the provision of a cardiac stimulating pulse to said atrial terminal.

18. The invention according to claim 16 wherein said circuit means includes atrial refractory means for inhibiting the response to the atrial sensing means signal for a certain atrial refractory period following either the provision of a cardiac stimulating pulse to said atrial terminal or the provision of an atrial sensing means signal and further includes ventricular refractory means for inhibiting the response to the ventricular sensing means signal for a certain ventricular refractory period following either the provision of a ventricular stimulating pulse to said ventricular terminal or the provision of a ventricular sensing means signal.

19. The invention according to claim 16 wherein said atrial pulse providing means includes first and second switch means and capacitance means coupled to said atrial terminal and means to charge said capacitance means through said first switch means and to discharge said capacitance means through said second switch means.

20. The invention according to claim 19 wherein said first switch means includes delay means to delay the charging of said capacitance means until after the discharge of said capacitance means.

21. The invention according to claim 16:
wherein said circuit means includes means for inhibiting any response of said ventricular sensing means for a certain time, less than said first time, following the provision of a cardiac stimulation pulse to said atrial terminal;
wherein said circuit means includes atrial refractory means for inhibiting the response to the atrial sensing means signal for a certain atrial refractory period following either the provision of a cardiac stimulating pulse to said atrial terminal or the provision of an atrial sensing means signal and further includes ventricular refractory means for inhibiting the response to the ventricular sensing means signal for a certain ventricular refractory period following either the provision of a ventricular stimulating pulse to said ventricular terminal or the provision of a ventricular sensing means signal;
wherein said atrial pulse providing means includes first and second switches and capacitance means coupled to said atrial terminal and means to charge said capacitance means through said first switch and to discharge said capacitance means through said second switch; and
wherein said first switch means includes delay means to delay the charging of said capacitance means until after the discharge of said capacitance means.

22. A cardiac pacemaker pulse generator comprising:
first sensing means adapted to being connected to the atrium of a heart for providing an atrial sense signal whenever a signal indicative of a natural atrial contraction occurs;
second sensing means adapted to being connected to the ventricle of said heart for providing a ventricular sense signal whenever a signal indicative of a natural ventricular contraction occurs;
first timing means for providing a first trigger signal at the expiration of a first constant defined time interval, and having means responsive to an atrial sense signal for commencing said first defined time interval;
second timing means for providing a second trigger signal at the expiration of a second constant defined time interval and having means responsive to a ventricular sense signal for commencing said second defined time interval;
first pulse generating means responsive to said first trigger signal for providing a ventricular stimulating pulse to the ventricle of the heart;
second pulse generating means responsive to said second trigger signal for providing an atrial stimulating pulse to the atrium of the heart;
and wherein:

said first timing means is further responsive to the provision of an atrial stimulating pulse for commencing said first constant defined time interval; and said second timing means is further responsive to the provision of ventricular stimulating pulse for commencing said second constant defined time interval;

whereby, a ventricular stimulating pulse is delivered unless a spontaneous ventricular depolarization is detected within said first constant defined time interval commenced by a preceding spontaneous atrial depolarization or atrial stimulating pulse and an atrial stimulating pulse is delivered unless a spontaneous atrial depolarization is detected within said second constant defined time interval commenced by a preceding spontaneous ventricular depolarization or ventricular stimulating pulse.

23. The invention according to claim 22 wherein further comprising blanking means for inhibiting any response of said second sensing means for a certain time, less than said first constant defined time interval, following the provision of an atrial stimulating pulse.

24. The invention according to claim 22 further comprising:

atrial refractory means for inhibiting the response of the first timing means for a certain atrial refractory period following either the provision of an atrial stimulating pulse or the provision of an atrial sense signal; and ventricular refractory means for inhibiting the response of the second timing means for a certain ventricular stimulating pulse or the provision of a ventricular sense signal.

25. The invention according to claim 22 further comprising:

blanking means for inhibiting any response of said second sensing means for a certain time, less than said first constant defined time interval, following the provision of an atrial stimulating pulse;

atrial refractory means for inhibiting the response of the first timing means for a certain atrial refractory period following either the provision of an atrial stimulating pulse or the provision of an atrial sense signal; and ventricular refractory means for inhibiting the response of the second timing means for a certain ventricular refractory period following either the provision of a ventricular stimulating pulse or the provision of a ventricular sense signal.

* * * * *

UNITED STATES PATENT AND TRADEMARK OFFICE
CERTIFICATE OF CORRECTION

PATENT NO. : 4,312,355
DATED : January 26, 1982
INVENTOR(S) : Hermann D. Funke

It is certified that error appears in the above-identified patent and that said Letters Patent are hereby corrected as shown below:

Column 3,
   Line 55, "Q" should be --$\bar{Q}$--;

Column 4,
   Line 5, "Q" should be --$\bar{Q}$--;

Line 49, "Q" should be --$\bar{Q}$--;

Column 5,
   Line 8, "Q" should be --$\bar{Q}$--.

Signed and Sealed this

Twenty-fourth Day of May 1983

[SEAL]

Attest:

DONALD J. QUIGG

Attesting Officer

Acting Commissioner of Patents and Trademarks